(12) United States Patent
Childers et al.

(10) Patent No.: US 7,816,362 B2
(45) Date of Patent: *Oct. 19, 2010

(54) SEROTONERGIC AGENTS

(75) Inventors: Wayne Everett Childers, New Hope, PA (US); Michael Kelly, Thousand Oaks, CA (US); Sharon Joy Rosenzweig-Lipson, East Brunswick, NJ (US)

(73) Assignee: Wyeth LLC, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/435,862

(22) Filed: May 5, 2009

(65) Prior Publication Data

US 2009/0215794 A1    Aug. 27, 2009

Related U.S. Application Data

(63) Continuation of application No. 11/330,907, filed on Jan. 11, 2006, now abandoned, which is a continuation of application No. 10/441,536, filed on May 20, 2003, now Pat. No. 7,026,320, which is a continuation of application No. 10/218,251, filed on Aug. 14, 2002, now Pat. No. 6,586,436, which is a continuation of application No. 10/010,575, filed on Nov. 13, 2001, now Pat. No. 6,469,007.

(60) Provisional application No. 60/253,301, filed on Nov. 28, 2000, provisional application No. 60/297,814, filed on Jun. 13, 2001.

(51) Int. Cl.
    *A61K 31/496* (2006.01)

(52) U.S. Cl. .................................. 514/253.11; 544/364

(58) Field of Classification Search ........................ None
    See application file for complete search history.

(56) References Cited

U.S. PATENT DOCUMENTS

| | | | |
|---|---|---|---|
| 5,532,244 A | 7/1996 | Wong et al. | |
| 5,532,250 A | 7/1996 | Wong et al. | |
| 5,532,264 A | 7/1996 | Wong et al. | |
| 5,532,268 A | 7/1996 | Wong et al. | |
| 5,538,992 A | 7/1996 | Wong et al. | |
| 5,552,429 A | 9/1996 | Wong et al. | |
| 5,710,149 A | 1/1998 | Cliffe et al. | |
| 5,756,532 A | 5/1998 | Stack et al. | |
| 5,776,969 A | 7/1998 | James | |
| 6,127,357 A | 10/2000 | Cliffe et al. | |
| 6,169,105 B1 | 1/2001 | Wong et al. | |
| 6,172,062 B1 | 1/2001 | Clark et al. | |
| 6,459,007 B1 | 10/2002 | Santi et al. | |
| 6,469,007 B2 | 10/2002 | Childers et al. | |
| 6,566,112 B2 | 5/2003 | Jones et al. | |
| 6,586,436 B2 | 7/2003 | Childers et al. | |
| 6,713,626 B2 | 3/2004 | Feigelson et al. | |
| 7,026,320 B2 | 4/2006 | Childers et al. | |
| 7,425,558 B2 * | 9/2008 | Rizzo et al. ............ 514/253.11 |
| 2003/0204087 A1 | 10/2003 | Chan et al. | |
| 2004/0230056 A1 | 11/2004 | Feigelson et al. | |
| 2005/0209245 A1 | 9/2005 | Chan et al. | |
| 2005/0215561 A1 | 9/2005 | Ghosh et al. | |

FOREIGN PATENT DOCUMENTS

| | | |
|---|---|---|
| EP | 0 512 755 | 11/1992 |
| EP | 0 687 472 | 12/1995 |
| EP | 0 792 649 | 9/1997 |
| WO | WO-94/13643 | 6/1994 |
| WO | WO-94/13644 | 6/1994 |
| WO | WO-94/13661 | 6/1994 |
| WO | WO-94/13676 | 6/1994 |
| WO | WO-94/13677 | 6/1994 |
| WO | WO-95/33725 | 12/1995 |
| WO | WO-95/33743 | 12/1995 |
| WO | WO-97/03982 | 2/1997 |
| WO | WO-02/44142 | 6/2002 |
| WO | WO-03/078396 | 9/2003 |
| WO | WO-03/078417 | 9/2003 |
| WO | WO-2004/082686 | 9/2004 |

OTHER PUBLICATIONS

Alexandre et al., 2006, "Early Life Blockage of 5-Hydroxytryptamine 1A Receptors Normalizes Sleep and Depression-Like Behavior in Adult Knock-Out Mice Lacking the Serotonin Transporter", J. of Neuroscience, 26(20):5554-5564.

Artigas et al., 1996, "Acceleration of the effect of selected antidepressant drugs in major depression by 5-HT1A antagonists", Trends Neurosci. 19(9):378-383.

(Continued)

*Primary Examiner*—Emily Bernhardt
(74) *Attorney, Agent, or Firm*—Jennifer Kispert; Ian J. S. Lodovice

(57) ABSTRACT

Novel piperazine derivatives are provided having the formula (III)

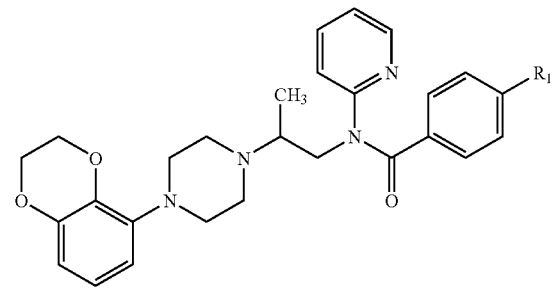

wherein $R_1$ is cyano, nitro, trifluoromethyl or halogen, or pharmaceutically acceptable acid addition salts thereof, which are useful as 5-$HT_{1A}$ receptor antagonists.

2 Claims, No Drawings

OTHER PUBLICATIONS

Azmitia, 2001, "Neuronal Instability: Implications for Rett's Syndrome", Brain & Development, 23:S1-S10.
Balant, et al., 1995, "Metabolic Considerations in Prodrug Design" *Burger's Medicinal Chemistry and Drug Discovery, Fifth Edition*, vol. 1, Wolff, ed., John Wiley & Sons, pp. 949-982.
Baldwin, 2004, "Sexual Dysfunction Associated with Antidepressant Drugs", Expert Opin. Drug Saf., 3(5):457-470.
Berends et al., 2005, "A Review of the Neuroprotective Properties of the 5-HT1A Receptor Agonist Repinotan HCl (BAY x 3702) in Ischemic Stroke", CNS Drug Reviews 11(4):379-402.
Beresford, et al., 2003, "Treatments for Stroke", Expert Opin. Emerging Drugs, 8(1):103-122.
Blackburn, 2004, "Serotonergic Agents and Parkinson's Disease", Drug Discovery Today: Therapeutic Strategies, 1(1):35-41.
Blanchard et al., 1997, "An Ethopharmacological Analysis of Selective Activation of 5-HT1A Receptors: The Mouse 5-HT1A Syndrome", Pharmacology Biochem. and Behavior, 57(4):897-908.
Boast et al., 1999, "5HT Antagonists Attenuate MK801-Impaired Radial Arm Maze Performance in Rats", Neurobiol. Learning Memory, 71:259-271.
Borg, et al., 2006, "Search for Correlations between Serotonin 5-$HT_{1A}$ Receptor Expression and Cognitive Functions—a Strategy in Translational Psychopharmacology", Psychopharmacology, 185:389-394.
Cao et al., 1998, "Tolerance to acute anxiolysis but no withdrawal anxiogenesis in mice treated chronically with 5-HT1A receptor antagonist, WAY 100635", Neuroscience and Biobehavioral Reviews, 23:247-257.
Cao, 1997, "Influence of 5-HT1A Receptor Antagonism on Plus-Maze Behaviour in Mice", Pharmacology Biochem. and Behavior, 58(2):593-603.
Carli et al., 1995, "(S)-WAY-100135, a 5-HT1A receptor antagonist, prevents the impairment of spatial learning caused by intrahippocampal scopolamine", European J. Pharmacology, 283:133-139.
Carli et al., 1997, "WAY 100635, a 5-$HT_{1A}$ Receptor Antagonist, Prevents the Impairment of Spatial Learning Caused by Intrahippocampal Administration of Scopolamine or 7-Chloro-Kynurenic Acid", Brain Res. 774:167-174.
Carli et al., 1999, "WAY 100635, a 5-$HT_{1A}$ receptor antagonist, prevents the impairment of spatial learning caused by blocade of hippocampal NMDA receptors", Neuropharmacol. 38:1165-1173.
Carli et al., 2000, "The 5-$HT_{1A}$ Receptor Agonist 8-OH-DPAT Reduces Rats' Accuracy of Attentional Performance and Enhances Impulsive Responding in a Five-Choice Serial Reaction Time Task: Role of Presynaptic 5-$HT_{1A}$ Receptors", Psychopharmacol., 149:259-268.
Cheeta et al., 2001, "The dorsal raphe nucleus is a crucial structure mediating nicotine's anxiolytic effects and the development of tolerance and withdrawal responses", Psychopharmacology, 155:78-85.
Childers, et al., 2005, "Synthesis and Biological Evaluation of Benzodioxanylpiperazine Derivatives as Potent Serotonin 5-$HT_{1A}$ Antagonists: The Discovery of Lecozotan", J. Med. Chem., 48:3467-3470.
Collinson et al., 1997, "On the elevated plus-maze the anxiolytic-like effects of the 5-HT(1A) agonist, 8-OH-DPAT, but not the anxiogenic-like effects of the 5-HT(1A) partial agonist, buspirone, are blocked by the 5-HT1A antagonist, WAY 100635", Psychopharmacology (Berl). 132(1):35-43.
Cryan et al., 1999, "Comparative effects of serotonergic agonists with varying efficacy at the 5-HT1A receptor on core body temperature: modification by the selective 5-HT1A receptor antagonist WAY 100635", J. Psychopharmacol., 13:278-283.
Dijk et al., 1995, "NMDA-induced glutamate and aspartate release from rat cortical pyramidal neurons; evidence for modulation by a 5-HT1A antagonist", British J. of Pharmacology, 115:1169-1174.
Dunlop, et al., 1998, "Characterization of 5-$HT_{1A}$ Receptor Functional Coupling in Cells Expressing the Human 5-$HT_{1A}$ Receptor as Assessed with the Cytosensor Microphysiometer", J. Pharmacol. Tox. Methods, 40:47-55 (1998).
Duxon et al., 2000, "Latency to paroxetine-induced anxiolysis in the rat is reduced by co-administration of the 5-HT1A receptor antagonist WAY100635", British J. of Pharmaco., 130:1713-1719.
Ellingrod, et al., 1996, "Letters: Reassessment of Nefazodone", Amer. Journal of Healt-System Pharmacy, 53(19):2339-2340, 2343.
Ellingrod, et al., 1996, "Nefazodone: A New Antidepressant", Am. J. Health Syst. Pharm., 52:2799-2812.
European Examination Report for European Patent Application No. 06736178.2 mailed Jul. 29, 2008.
Fletcher et al., 1996, "Electrophysiological, biochemical, neurohormonal and behavioural studies with WAY-100635, a potent, selective and silent 5-HT1A receptor antagonist", Behav. Brain Res., 73:337-353.
Gudelsky et al., 1986, "Thermoregulatory responses to serotonin (5-HT) receptor stimulation in the rat", Neuropharmacology, 25(12):1307-1313.
Harder et al., 2000, "The 5-HT1A antagonist, WAY 100 635, alleviates cognitive impairments induced by dizocilpine (MK-801) in monkeys", Neuropharmacol., 39:547-552.
Hjorth et al., 1997, "WAY 100653-induced Augmentation of the 5-HT-elevating Action of Citalopram: Relative Importance of the Dose of the 5-HT1A Auto)receptor Blocker Versus that of the 5-HT Reuptake Inhibitor", Neuropharmacology, 36(4/5):461-465.
Hollander, et al., 1992, "Yohimbine Treatment of Sexual Side Effects Induced by Serotonin Reuptake Blockers", J. Clin Psychiatry, 53(6):207-209.
Hughes et al., 1991, "Symptoms of Tobacco Withdrawal", Arch. Gen. Psychiatry 48:52-59.
Hutson et al, 1988, "Evidence that the hyperphagic response to 8-OH-DPAT is mediated by 5-HT1A receptors", European J. of Pharmacology 150:361-366.
Jankovic, 2006, "An Update on the Treatment of Parkinson's Disease", Mount Sinai Journal of Medicine, 73:682-689.
Jones, et al, 2002, "The Medical Benefit of 5-HT Research", Pharmacology Biochemistry and Behavior, 71:555-568.
Joordens et al., 1998, "The effects of 5-HT1A receptor agonists, 5-HT1A receptor antagonists and their interaction on the fear-potentiated startle response", Psychopharmacol., 139:383-390.
Jorgensen et al., 1999, "Adrenocorticotropic Hormone Secretion in Rats Induced by Stimulation with Serotonergic Compounds", J. of Neuroendocrinology, 11:283-290.
Kakizaki et al., 2001, Effects of WAY100635, a selective 5-HT1A receptor antagonist on the micturition-reflex pathway in the rat:, Am. J. Physiol. Regul. Integr. Comp. Physiol., 280(5):R1407-1413.
Kalkman et al., 1995, "RU 24969-induced locomotion in rats is mediated by 5-HT1A receptors", Naunyn Schmiedeberg's Arch. Pharmacol., 352:583-584.
Kelly, et al., 2006,"A Randomized Double-Blind 12-Week Study of Quetiapine, Risperidone or Fluphenazine on Sexual Functioning in People with Schizophrenia", Psychoneuroendocrino, 31(3):340-346.
Kenny et al., 2000, "Anxiogenic effects of nicotine in the dorsal hippocampus are mediated by 5-HT1A and not by muscarinic M1 receptors", Neuropharmacology 39:300-307.
Kenny et al., 2001, "Nicotine regulates 5-HT1A receptor gene expression in the cerebral cortex and dorsal hippocampus", Eur. J. Neurosci. 13:1267-1271.
Killcross et al., 1997, "WAY100635 and latent inhibition in the rat: selective effects at preexposure", Behav. Brain Res., 88(1):51-57.
Kishitake, 2005, "Effects of 5-HT1A -Receptor Agonist, 8-OH-DPAT, and GABAB- Receptor Agonist, Baclofen, on Lordosis in Female Rats with Lesions in Either the Dorsal Raphe Nucleus or Septum", J. Pharmacol. Sci., 98:419-424.
Krebs-Thomson et al., 1996, "The role of 5-HT1A receptors in the locomotor-suppressant effects of LSD: WAY-100635 studies of 8-OH-DPAT, DOI and LSD in rats", Behav. Pharmacol., 7:551-559.
Lead Discovery. 2002. "Male and Female Sexual Dysfunction: Blockbuster Indication for Multiple Pharmacological Targets." Availabale at www.leaddiscovery.co.uk/dossiers/MDI002/Sexual%20dysfunction.htm.
Lin et al., 2002, "Melatonin potentiates 5-HT1A receptor activation in rat hypothalamus and results in hypothermia", J. of Pineal Research 33:14-19.

McVary et al., 1997, "Sexual dysfunction in the diabetic BB/WOR rat: a role of central neuropathy", Am. J. Physiol. Regul. Integr. Comp. Physiol., 272:R259-267.

Mendelson et al., 1993, "5-HT1A receptor agonists induce anterograde amnesia in mice through a postsynaptic mechanism", European J. of Pharmacology, 236:177-182.

Meneses et al., 1999, "5-HT1A Receptors Modulate the Consolidation of Learning in Normal and Cognitively Impaired Rats", Neurobiology of Learning and Memory, 71:207-218.

Merck Manual, Sixteenth Edition, 1992, "Disorders of Movement: Extrapyramidal and Cerebellar", Merck Research Laboratories, Rahway, N.J., pp. 1495-1500; see p. 1497.

Millan et al., 1998, "WAY 100,635 enhances both the 'antidepressant' actions of duloxetine and its influence on dialysate levels of serotonin in frontal cortex", European J. of Pharmaco. 341:165-167.

Newman-Tancredi, et al., 1998, "Agonist and Antagonist Actions of Antipsychotic Agents at 5-$HT_{1A}$ Receptors: a [$35_S$]GTP$\gamma$S Binding Study", European Journal of Pharmacology, 355:245-256.

Nielsen, et al,. 1988, "Glycolamide Esters as Biolabile Prodrugs of Carboxylic Acid Agents: Synthesis, Stability, Bioconversion, and Physiochemical Properties", Journal of Pharmaceutical Sciences, 77(4):285-298.

Norden, 1994, "Buspirone Treatment of Sexual Dysfunction Associated with Selective Serotonin Re-Uptake Inhibitors", Depression, 2:109-112.

Office Action citing prior art references issued for AR035603A1, dated Jan. 13, 2008.

Ohno et al., 1993, "Working memory deficits induced by intrahippocampal administration of 8-OH-DPAT, a 5-HT1A receptor agonist, in the rat", European J. of Pharmacology, 234:29-34.

Rasmussen et al., 1997, "Nicotine withdrawal leads to increased sensitivity of serotonergic neurons to the 5-HT1A agonist 8-OH-DPAT", Psychopharmacology, 133:343-346.

Rasmussen et al., 2000, "The Novel 5-Hydroxytryptamine1A Antagonist LY426965: Effects on Nicotine Withdrawal and Interactions with Fluoxetine", J. Pharmacol. Exp. Therapeutics, 294:688-700.

Robichaud, et al., 2000, "Chapter 2: Recent Advances in Selective Serotonin Receptor Modulation", Annual Reports in Med. Chem., Nov. 20, 2000, pp. 11-20.

Romero et al., 1996, "The 5-HT1A antagonist WAY-100635 selectively potentiates the presynaptic effects of serotonergic antidepressants in rat brain", Neuroscience Letters, 219:123-126.

Rosen et al., 1999, "Effects of SSRIs on Sexual Function: A Critical Review", J. Clin. Psychopharmacol., 19:67-85.

Schechter et al., 2002, "The Potential Utility of 5-HT1A Receptor Antagonists in the Treatment of Cognitive Dysfunction Associated with Alzheimer's Disease", Current Pharmaceutical Design, 8:139-145.

Schechter et al., 2005, "Lecozotan (SRA-333): A selective Serotonin 1A Receptor Antagonist That Enhances the Stimulated Release of Glutamate and Acetylcholine in the Hippocampus and Possesses Cognitive-Enhancing Properties", J. of Pharmacology and Experimental Therapeutics, 314:1274-1289.

Schenk, 2000, "Effects of the serotonin 5-HT2 antagonist, ritanserin, and the serotonin 5-HT1A antagonist, WAY 100635, on cocaine-seeking in rats", Pharmacol. Biochem. Behav., 67:3630369.

Smart et al., 2001, "WAY-100635, a specific 5-HT1A antagonist, can increase the responsiveness of the mammalian circadian pacemaker to photic stimuli", Neurosci. Lett., 305:33-36.

Smith, et al., 1990, "Effects of Four-Beta-Adrenergic Receptor Antagonists on Male Rat Sexual Behavior", Pharmacol. Biochem. Behav., 36(4):713-717.

Sramek et al., 2002, "Generalised Anxiety Disorder, Treatment Options", Drugs, 62(11):1635-1648.

Stimmel, et al., 1997, "Mirtazapine: An Antidepressant with Noradrenergic and Specific Serotonergic Effects", Pharmacotherapy, 17(1):10-21.

Sukoff Rizzo, et al., Society for Neuroscience Abstract #559.4 (2005).

Taylor, et al., 2005, "Strategies for Managing Antidepressant-Induced Sexual Dysfunction: Systematic Review of Randomised Controlled Trials", Journal of Affective Disorders, 88:241-254.

Testa, et al., 2001, "Effect of Different 5-Hydroxytryptamine Receptor Subtype Antagonists on the Micturition Reflex in Rats", BJU International, 87:256-264.

Van Den Hooff et al., 1991, "Electrophysiology of the 5-HT1A ligand MDL 73005EF in the rat hippocampal slice", European J. Pharmacology, 196:291-298.

Van Steen, et al., 1994, "Structure-Affinity Relationship Studies on 5-$HT_{1A}$ Receptor Ligands. 2. Heterobicyclic Phenylpiperazines with N4-Aralkyl Substituents", J. Med. Chem., 37:2761-2773.

Vicentic et al., 1998, "WAY-100635 inhibits 8-OH-DPAT-stimulated oxytocin, ACTH and corticosterone, but not prolactin secretion", Eur. J. Pharmacol., 346:261-266.

Volpicelli, "Medicatins for Alcoholism Treatment", http://www.tgorski.com/Medication/medications_for_alcoholism_treatment.htm; posted Mar. 21, 2002; printed Oct. 23, 2007; pp. 1-17.

Waldinger, 2006, "Emerging drugs for premature ejaculation", Expert Opin. Emerging Drugs, 11:99-109, see p. 101.

Wilen, et al., 1977, Strategies in Optical Resolutions, Tetrahedron, 33:2725.

Wood, et al., 2002, "Therapeutic Potential of Serotonin Antagonists in Depressive Disorders", Expert Opin. Investig. Drugs, 11(4):457-467.

Zhou et al., 1998, "Additive Reduction of Alcohol Drinking by 5-HT1A Antagonist WAY 100635 and Serotonin Uptake Blocker Fluoxetine in Alcohol-Preferring P Rats", Alcohol. Clin. Exp. Res., 22:266-269.

* cited by examiner

SEROTONERGIC AGENTS

This is a continuation of U.S. application Ser. No. 11/330,907 filed on Jan. 11, 2006, which is a continuation of U.S. application Ser. No. 10/441,536 filed on May 20, 2003, which is a continuation of co-pending application Ser. No. 10/218,251, filed on Aug. 14, 2002, which is a continuation of application Ser. No. 10/010,575, filed Nov. 13, 2001, which claims the benefit of provisional application Ser. No. 60/253,301, filed Nov. 28, 2000 and provisional application Ser. No. 60/297,814, filed Jun. 13, 2001, each of which is hereby incorporated by reference in their entirety.

FIELD OF THE INVENTION

This invention relates to novel piperazine derivatives, to their use and to pharmaceutical compositions containing them. The novel compounds are useful as $5\text{-HT}_{1A}$ binding agents, particularly as $5\text{-HT}_{1A}$ receptor antagonists.

BACKGROUND

U.S. Pat. No. 6,127,357 discloses compounds of the general formula (I):

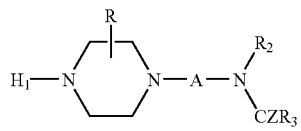

(I)

and pharmaceutically acceptable acid addition salts thereof wherein:

A is alkylene chain of 2 to 4 carbon atoms optionally substituted by one or more lower alkyl groups, Z is oxygen or sulfur, R is H or lower alkyl, $R^1$ is a mono or bicyclic aryl or heteroaryl radical, $R^2$ is a mono or bicyclic heteroaryl radical, and $R^3$ is hydrogen, lower alkyl, cycloalkyl, cycloalkenyl, cycloalkyl(lower)alkyl, aryl, aryl(lower)alkyl, heteroaryl, heteroaryl(lower)alkyl, a group of formula —$NR^4R^5$ [where $R^4$ is hydrogen, lower alkyl, aryl or aryl(lower)alkyl and $R^5$ is hydrogen, lower alkyl, —CO(lower)alkyl, aryl, -Coaryl, aryl(lower)alkyl, cycloalkyl, or cycloalkyl-(lower)alkyl or $R^4$ and $R^5$ together with the nitrogen atom to which they are both attached represent a saturated hetrocyclic ring which may contain a further heteroatom], or a group of formula $OR^6$ [where $R^6$ is lower alkyl, cycloalkyl, cycloalkyl(lower)alkyl, aryl, aryl (lower)alkyl, heteroaryl or heteroaryl(lower)alkyl].

WO 97/03982 discloses compounds of the general formula (II):

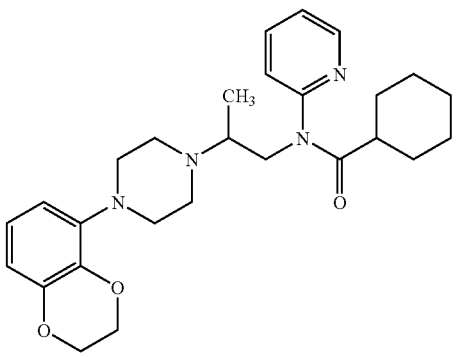

(II)

including enantiomers and the pharmaceutically acceptable acid addition salts thereof.

The compounds of formula (II) fall within the disclosure of U.S. Pat. No. 6,127,357 but are not specifically disclosed therein Compounds of Formula II were taught to have potent $5\text{-HT}_{1A}$ antagonist activity in vivo when administered by the oral route.

DETAILED DESCRIPTION OF THE INVENTION

Novel compounds of the invention have the structural formula (III)

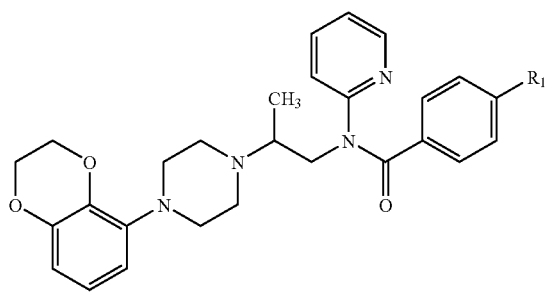

(III)

wherein $R_1$ is cyano, nitro, trifluoromethyl or halogen, or pharmaceutically acceptable acid addition salts thereof.

Halogen, as used herein, refers to chlorine, fluorine, bromine and iodine.

The compounds of Formula III contain an asymmetric carbon atom. Accordingly, they may exist in different stereoisomeric forms. In some preferred embodiments the R stereoisomer (Formula IIIa) is preferred.

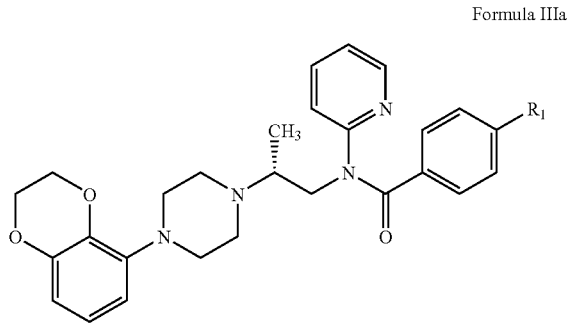

Formula IIIa

In accordance with some embodiments of the invention, the (R) stereoisomer is substantially free of the (S) stereoisomer. Substantially free, as used herein means that the compound is made up of a significantly greater proportion of its (R) stereoisomer than the (S) stereoisomer. In preferred embodiments the compound is made up of at least about 90% by weight of its (R) stereoisomer and about 10% by weight or less of its (S) stereoisomer. In other embodiments of the invention, the compound is made up of at least about 99% by weight of its (S) stereoisomer and about 1% by weight or less of the (R) stereoisomer. Preferred stereoisomers may be isolated from racemic mixtures by any method known to those skilled in the art, including high performance liquid chromatography (HPLC) and the formation and crystallization of chiral salts. See, for example, Jacques, et al., *Enantiomers, Racemates and Resolutions* (Wiley Interscience, New York, 1981); Wilen, S. H, et al., *Tetrahedron* 33:2725 (1977); Eliel, E. L. Stereochemistry of Carbon Compounds (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The most preferred compounds of the invention are (R)-4-Cyano-N-{2-[4-(2,3-dihydro-benzo[1,4]dioxin-5-yl)-piperazin-1-yl]propyl}-N-pyridin-2-yl-benzamide; and pharmaceutically acceptable acid addition salts thereof.

The pharmaceutically acceptable salts are the acid addition salts which can be formed from a compound of the above general formula and a pharmaceutically acceptable acid such as, for example, benzoic, phosphoric, sulfuric, hydrochloric, hydrobromic, citric, maleic, malic, mandelic, mucic, nitric, fumaric, succinic, tartaric, acetic, lactic, pamoic, pantothenic, benzenesulfonic, or methanesulfonic acid. In some embodiments of the invention the preferred acid addition salt is hydrochloric acid.

The compounds of the present invention can be prepared by known methods from known starting materials which are available by conventional methods. For example the compounds may be prepared by the general methods disclosed in EP-A-0512755 and WO 97/03982.

Such disclosed methods include acylating an amine of formula (IV) with a known benzoyl chloride (V) or an alternative acylating derivative thereof. Examples of acylating derivatives include the acid anhydride, imidazolides (e.g. obtained form carbonyldiimidazole), or activated esters.

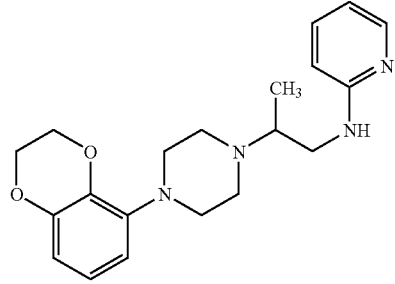

(IV)

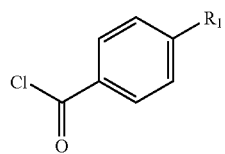

(V)

wherein $R_1$ is cyano, halogen, trifluoromethyl or nitro.

Novel compounds of the present invention are potent 5-$HT_{1A}$ binding agents which selectively binds to the 5-$HT_{1A}$ receptor. Furthermore, the novel compounds of the invention are 5-$HT_{1A}$ receptor antagonists when tested by standard pharmacological procedures.

In addition, the novel compounds of formula (III) are unique from previously disclosed 5$HT_{1A}$ receptor antagonists in that they possess a superior duration of action as a 5-$HT_{1A}$ receptor antagonist when administered in vivo.

EXAMPLES

The present invention is illustrated by reference to the following example. Those skilled in the art of organic synthesis may be aware of still other synthetic routes to the invention compound. The reagents and intermediates used herein are either commercially available or prepared according to standard literature procedures.

Example 1

(R)-4-Cyano-N-{2-[4-(2,3-Dihydro-Benzo[1,4]dioxin-5-yl]piperazin-1-yl]-Propyl}-N-Pyridin-2-yl-Benzamide A solution of {(R)-2-[4-(2,3-dihydrobenzo[1,4]dioxin-5-yl)piperazin-1-yl]propyl}-pyridin-2-ylamine (0.846 g, 2.38 mmol) in dichloromethane (20 mL) was treated at 0° C. with the dropwise addition of a dichloromethane solution of 4-cyanobenzoyl chloride (1.1 equivalents, 2.63 mmol in 5 mL). After stirring for 16 hours the mixture was poured onto hexane (100 mL) to precipitate the titled compound as its monohydrochloride salt (white solid, 1.2 g, 97% yield), which was recrystallized from dichloromethanelhexane.

MS (+) 484 (M+H)$^+$.

m.p. 239-240° C.

[α]25/D=+56 (c=0.6, MeOH)

Elemental Analysis for: $C_{28}H_9N_5O_3 \cdot 1.0HCl$

Calculated: C, 64.67; H, 5.81; N, 13.47:

Found: C, 64.69; H, 5.93; N, 13.52:

In order to demonstrate the superior duration of action of the compounds of formula (III), Example 1 was compared to representative compounds of U.S. Pat. No. 6,127,357 and WO 97/03892.

Representative compounds of U.S. Pat. No. 6,127,357 possess a cyclohexylamide moiety and a 2-methoxyphenylpiperazine grouping. The most potent example of this general structure (and the most potent compound taught in U.S. Pat. No. 6,127,357) is compound A, described as "example 3" in U.S. Pat. No. 6,127,357. The only other class of compounds in U.S. Pat. No. 6,127,357 for which data are given is that which possess a cyclohexylamide moiety and a benzodioxinylpiperazine grouping ("Example 17" in U.S. Pat. No. 6,127,357). A small subset of this class of compounds is specifically claimed in WO97/03892, with the preferred compound being compound B ("example A1" in WO97/03892). Therefore, these two preferred examples from EP-A-0512755 and WO 97/03892 have been chosen as representatives for comparison to the compounds of formula (III).

Compound A

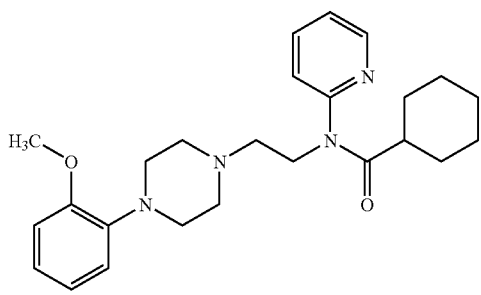

("Example 3" from U.S. Pat. No. 6,127,357)

Compound B

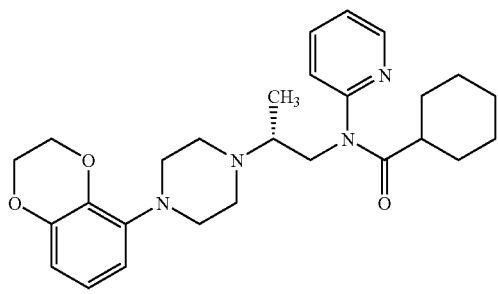

("Example A1" from WO 97/03892)

Example 2

Binding Profile

Compounds were tested for binding to cloned human 5-HT$_{1A}$ receptors stably transfected into CHO cells using [$^3$H]8-OH-DPAT as the 5-HT$_{1A}$ radioligand (according to general procedure described in J. Dunlop et al., *J. Pharmacol. Tox. Methods*, 40, 47-55 (1998)). As shown in Table 1, compounds of the present invention display high affinity for the 5HT$_{1A}$ receptor.

Example 3

In Vitro Functional Activity

A clonal cell line stably transfected with the human 5-HT$_{1A}$ receptor was utilized to determine the intrinsic activity of compounds (according to the general procedure described in J. Dunlop et al., *J. Pharamcol. Tox. Methods*, 40, 47-55 (1998)). Data are provided in Table 1. As shown in Table 1, compounds of the present invention antagonized the ability of 10 nM 8-OH-DPAT to inhibit forskolin-stimulated cAMP production in a concentration-related fashion.

TABLE 1

| Compound | 5-HT$_{1A}$ Affinity Ki (nm) | 5-HT$_{1A}$ Antagonist Activity cAMP Assay IC$_{50}$ (nM) |
|---|---|---|
| Example 1 | 1.6 | 25 |
| Compound A | 0.96 | 7 |
| Compound B | 0.97 | 20 |

Example 4

In Vivo Functional Activity

The ability of the compounds to function in vivo as 5-HT$_{1A}$ antagonists was assessed in rats using a Fixed Responding Model (D. Blackman, in "Operant Conditioning: An Experimental Analysis of Behavior", J. Butcher, ed., Methuen and Co., Ltd., London). In this model rats are trained to respond (lever pressing) under a fixed-ratio 30 schedule of food presentation in order to receive a food pellet reinforcer. Administration of the 5-HT$_{1A}$ agonist 8-OH-DPAT reduces the control response rate (assessed by administration of vehicle placebo). The 5-HT$_{1A}$ antagonist activity of a test compound is determined by measuring its ability to antagonize this agonist-induced decrease in response rate. A full antagonist effect is considered one in which the test compound completely reverses the agonist-induced response rate, returning it to control levels. The data given in Table 2 demonstrate that a 1 mg/kg dose of the compound of Example 1 completely reverses the decrease in response rate induced by administration of a 0.3 mg/kg dose of 8-OH-DPAT. Thus, compounds of the present invention function as 5-HT$_{1A}$ antagonists in vivo.

TABLE 2

| Response Rate (responses/second) | | |
|---|---|---|
| Vehicle (Control) | 8-OH-DPAT (0.3 mg/kg sc) | 8-OH-DPAT (0.3 mg/kg sc) + Example 1 (1 mg/kg sc) |
| 2.4 ± 0.5 | 0.5 ± 0.2 | 2.5 ± 0.2 |

Example 5

Duration of Action In Vivo

The duration of action in the Fixed Responding Model was assessed by pre-treating animals with test compound and then challenging with a 0.3 mg/kg dose of the 5-HT$_{1A}$ agonist 8-OH-DPAT at various time intervals after the administration of test compound. All drug and vehicle administrations were made by the subcutaneous route. Doses of the test compounds selected for comparison were those which caused a ten-fold shift in the 8-OH-DPAT dose-response curve when administered 30 minutes prior to agonist. The doses selected for the duration of action comparison are listed in Table 3.

TABLE 3

| Test Compound | Dose Which Shifts Agonist Dose-response Curve by 10-fold (mg/kg, sc) |
|---|---|
| Compound A (FIG. 1) | 0.03 |
| Compound B (FIG. 1) | 0.1 |
| Example 1 | 1.0 |

Data are presented for pretreatment of the animals with test compound at 0.5 hours, 2 hours, and 4 hours prior to administration of a 0.3 mg/kg dose of 8-OH-DPAT. Results are normalized to control values, with 100% being the control response rate observed when vehicle is administered rather than the agonist 8-OH-DPAT.

TABLE 4

| Compound | % Response Rate | | |
| --- | --- | --- | --- |
| | 0.5 hour pretreatment | 2 hour pretreatment | 4 hour pretreatment |
| Compound A + 8-OH-DPAT | 90 ± 3 | 55 ± 28 | 41 ± 26 |
| Control + 8-OH-DPAT | 23 ± 9 | 3 ± 1 | 3 ± 1 |
| Compound B + 8-OH-DPAT | 100 ± 11 | 71 ± 12 | 27 ± 14 |
| Control + 8-OH-DPAT | 21 ± 9 | 42 ± 6 | 42 ± 6 |
| Example 1 + 8-OH-DPAT | 100 ± 7 | 118 ± 13 | 99 ± 16 |
| Control + 8-OH-DPAT | 29 ± 6 | 35 ± 10 | 35 ± 10 |

As can be seen from Table 4, all three test compounds (Compound A, B and Example 1) completely antagonize the agonist-induced decrease in responding 30 minutes after their administration, returning the response rate to control levels. However, when agonist is given 2 hours following test drug administration (Column 3), the 5-$HT_{1A}$ antagonist effects of compounds A and B no longer return the response rate to control levels while Example 1 still displays complete 5-$HT_{1A}$ antagonist effects. By four hours post-administration (Column 4), the 5-$HT_{1A}$ antagonist effects of Compounds A and B are completely lost, while Example 1 continues to provide complete antagonism of the agonist-induced decrease in response rate. Thus, the duration of action of Example 1 is longer than 4 hours, while those of Compounds A and B are somewhere between 30 minutes and 2 hours.

The increased duration of action of the novel compounds of the present invention, compared to that of the classes of compounds disclosed in U.S. Pat. No. 6,127,357 and WO 97/03892 is particularly advantageous in that a smaller number of doses of the compound can be administered to produce a similar therapeutic effect.

Compounds of the present invention may be used to treat a subject suffering from CNS disorders such as schizophrenia, (and other psychotic disorders such as paranoia and manodepressive illness), Parkinson's disease and other motor disorders, anxiety (e.g. generalized anxiety disorders, panic attacks, and obsessive compulsive disorders), depression (such as by the potentiation of serotonin reuptake inhibitors and serotonin norepinephrine reuptake inhibitors), Tourette's syndrome, migraine, autism, attention deficit disorders and hyperactivity disorders. Compounds of the present invention may also be useful for the treatment of sleep disorders, social phobias, pain, thermoregulatory disorders, endocrine disorders, urinary incontinence, vasospasm, stroke, eating disorders such as for example obesity, anorexia and bulimia, sexual dysfunction, and the treatment of alcohol, drug and nicotine withdrawal.

Compounds of the present invention are also useful for the treatment of cognitive dysfunction. Thus, compounds of the present invention may be useful for the treatment of cognitive dysfunction associated with mild cognitive impairment (MCI)) Alzheimer's disease and other dementias including Lewy Body, vascular, and post stroke dementias. Cognitive dysfunction associated with surgical procedures, traumatic brain injury or stroke may also be treated in accordance with the present invention. Further, compounds of the present invention may be useful for the treatment of diseases in which cognitive dysfunction is a co-morbidity such as, for example, Parkinson's disease, autism and attention deficit disorders.

"Provided", as used herein with respect to providing a compound or substance covered by this invention, means either directly administering such a compound or substance, or administering a prodrug, derivative, or analog which will form an equivalent amount of the compound or substance within the body. Prodrugs can be prepared such as described in *Design of Prodrugs*, Bundgaard, H ed., (Elsevier, N.Y. 1985); *Prodrugs as Novel Drug Delivery Systems*, Higuchi, T. and Stella, V. eds, (American Chemical Society, Washington, D.C. 1975); *Design of Biopharmaceutical Properties through Prodrugs and Analogs*, Roche, E. ed., (American Pharmaceutical Association Academy of Pharmaceutical Sciences, Washington, D.C., 1977); and Metabolic Considerations in Prodrug Design, Balant, L. P. and Doelker, E. in *Burger's Medicinal Chemistry amd Drug Discovery*, Fifth Edition, Wolff, M., ed, Volume 1, pages 949-982, (John Wiley & Sons, Inc. 1995).

The compounds of the present invention may be administered orally or parentally, neat or in combination with conventional pharmaceutical carriers. Applicable solid carriers can include one or more substances which may also act as flavoring agents, lubricants, solubilizers, suspending agents, fillers, glidants, compression aids, binders, tablet-disintegrating agents or encapsulating materials. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets may contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration. Liquid pharmaceutical compositions which are sterile solutions or suspensions can be utilized by, for example, intramuscular, intraperitoneal or subcutaneous injection. Sterile solutions can also be administered intravenously. Oral administration may be either in liquid or solid composition form. Preferably, the pharmaceutical compositions containing the present compounds are in unit dosage form, e.g., as tablets or capsules. In such form, the composition is sub-divided in unit dosages containing appropriate quantities of the active ingredients. The unit dosage forms can be packaged compositions, for example, packaged powders, vials, ampoules, prefilled syringes or sachets containing liquids. Alternatively, the unit dosage form can be, for example, a capsule or tablet itself, or it can be the appropriate number of any such compositions in package form. The therapeutically effective dosage to be used may be varied or adjusted by the physician and generally ranges from 0.5 mg to 750 mg, according to the specific condition(s) being treated and the size, age and response pattern of the patient.

The present invention may be embodied in other specific forms without departing from the spirit and essential attributes thereof and accordingly, reference should be made to the appended claims, rather than to the foregoing specification, as indicating the scope of the invention.

What is claimed:

1. A method for potentiating the effects of a serotonin reuptake inhibitor in a patient in need thereof, the method comprising providing to the patient a therapeutically effective amount of a compound of formula (III):

(III)

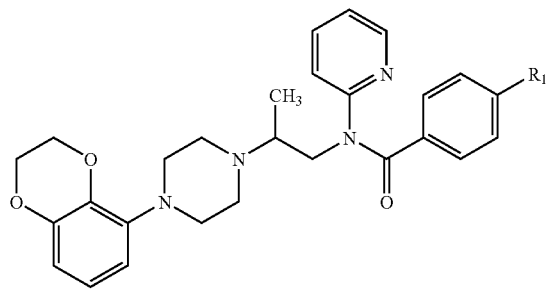

wherein $R_1$ is cyano, nitro, trifluoromethyl or halogen, or a pharmaceutically acceptable acid addition salt thereof.

2. The method of claim 1, wherein the compound is (R)-4-cyano-N-{2-[4-(2,3-dihydro-benzo[1,4]dioxin-5-yl)piperazine-1-yl]-propyl}-N-pyridin-2-yl-benzamide.

* * * * *